(12) United States Patent
Hietala

(10) Patent No.: US 7,435,225 B2
(45) Date of Patent: Oct. 14, 2008

(54) METHOD AND ARRANGEMENT FOR MEASURING BREATH GASES OF A PATIENT

(75) Inventor: Mika Hietala, Espoo (FI)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/562,493

(22) Filed: Nov. 22, 2006

(65) Prior Publication Data
US 2008/0119754 A1   May 22, 2008

(51) Int. Cl.
    *A61B 5/08* (2006.01)
(52) U.S. Cl. ................................ 600/532; 73/23.24
(58) Field of Classification Search ............... 600/532, 600/528, 538, 543, 587, 533, 529; 73/23.2, 73/861, 1.16, 23.21, 23.23, 23.24, 23.3, 23.36, 73/23.37, 23.4, 23.41, 23.42; 33/512; 422/84; 128/200.26, 204.22, 204.23, 200.15
See application file for complete search history.

(56) References Cited

U.S. PATENT DOCUMENTS

| | | | | |
|---|---|---|---|---|
| 4,233,842 A | * | 11/1980 | Raemer et al. | 73/861.04 |
| 5,042,501 A | * | 8/1991 | Kenny et al. | 600/532 |
| 5,129,401 A | * | 7/1992 | Corenman et al. | 600/529 |
| 5,363,857 A | * | 11/1994 | Howard | 600/531 |
| 5,398,695 A | * | 3/1995 | Anderson et al. | 600/532 |
| 6,029,664 A | * | 2/2000 | Zdrojkowski et al. | 128/204.23 |
| 6,325,978 B1 | * | 12/2001 | Labuda et al. | 422/84 |

OTHER PUBLICATIONS

Michael S. Levine, A respiration-modulated personal air sampling pump, 1994, Appl. Occup. Environ. Hyg. (Dec. 1994)☐☐☐☐.*

* cited by examiner

*Primary Examiner*—Charles A. Marmor, II
*Assistant Examiner*—Anita Saidi
(74) *Attorney, Agent, or Firm*—Andrus, Sceales, Starke & Sawall, LLP

(57) ABSTRACT

Method and arrangement for measuring breath gases of a patient in which the patient is connected to a breath gas unit by using a sampling line to enable flowing a sample of the breathing gases with a pre-determined sample flow rate to the breath gas measuring unit. The sample flow rate is adjusted in case it is not within limits set by the patient's breathing rate.

14 Claims, 2 Drawing Sheets

METHOD AND ARRANGEMENT FOR MEASURING BREATH GASES OF A PATIENT

BACKGROUND

The invention relates to measuring of breath gases of a patient. The patient's breath gases are measured for example in connection with a ventilation procedure carried out with the patient. The term ventilation covers here both ventilation procedures and also anesthesia procedures carried out with the patient.

A widely known way to measure breathing gases from the patient is to use sidestream technique. In this technique a ventilator is connected with ventilator tubes to the patient. Y-piece is connected to the airway adapter, which includes sampling line connector. Then there is a filter and intubation tube. Breath gas measuring unit draws a small amount of breathing air from the airway adapter using a pump. Air flows through the sampling line to the water trap, which removes water and mucus from the air. The air flows to the gas sensor, which measures one or more breath gases. Then there is a sample flow measurement unit and a pump. The CPU determines the gas concentrations based on the sensor signal(s). It also determines the sample flow and controls the pump according to the measurement result.

In this known technique normal way to implement sample flow control is to use a constant sample flow rate, which means that regardless of the situation the sample flow rate is tried to keep constant. The amount of sample flow rate is determined to be high enough for the maximum specified breathing rate that the device is enabled to measure.

The main drawbacks in the constant sample flow rate can be described as follows.

Because the sample flow rate may be higher than needed more water and mucus are drawn from the breathing circuit than it is necessary to achieve good measurement accuracy. Because of that the lifetime of the sampling line and water trap gets shorter. Also there are more occlusion situations than in the case of smaller sample flow rate.

The high sample flow shortens the lifetime of the pump. Also the noise generated by the pump is proportional to the load of the pump.

While using unnecessary high flow sample rate, in case of anesthesia the device draws unnecessary amount of expensive anesthetic gases from the ventilator circuit.

SUMMARY

The object of the invention is to provide a simple and practical method by which the disadvantages of the prior art technique can be eliminated. The main idea in the invention is that the invention uses a dynamic measurement, i.e. the sample flow rate is adjusted in case it is not within limits set by the patient's breathing rate.

The invention gives advantages compared to traditional constant sample flow rate. There is less water and mucus drawn from the patient ventilator circuit because the sample flow rate is on the average smaller than in traditional flow control. This means less occlusion situations and longer lifetime for sampling lines and water traps, which means cost savings for the user. Also when the sample flow rate is on the average small, the amount of expensive anesthetic gases drawn from the patient ventilator circuit is smaller (if gas circulation is not in use), which also gives cost savings for the user. Gas circulation causes potential contamination risks so it wouldn't be necessary to use it any more if the sample flow rate is small enough. The lifetime of the sample pump increases as its average load decreases. Also the noise generated by the pump decreases, which is important for the user.

BRIEF DESCRIPTION OF THE DRAWINGS

In the following the invention will be described in greater detail by means of the drawing, in which.

DETAILED DESCRIPTION OF THE DRAWINGS

Figure 1:
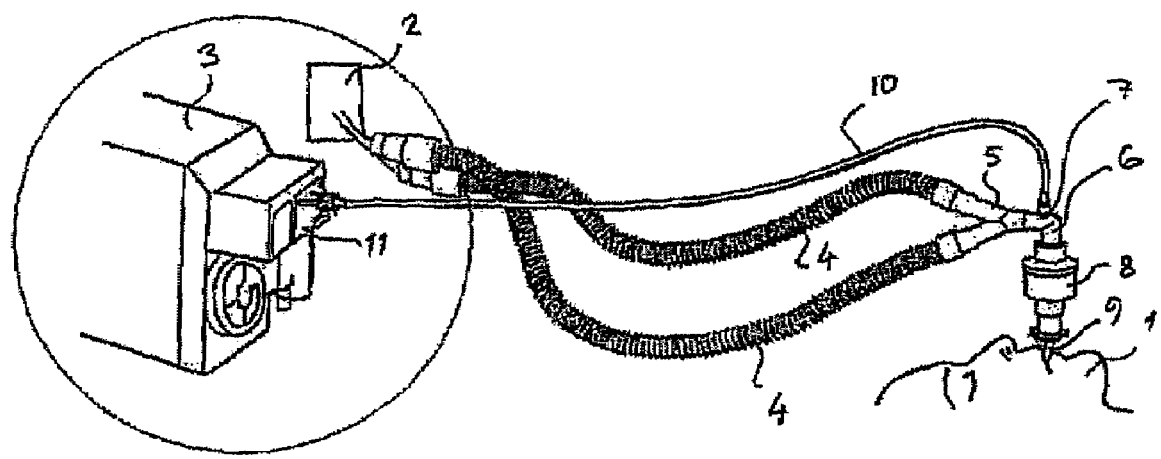
FIG. 1 shows principally the basic parts of the arrangement used for patient connection and patient's breath gas measuring proceedings.

FIG. 1 shows a general way to connect a patient 1 to a ventilator 2 and to a breath gas measuring unit 3. The ventilator 2 is connected with ventilator tubes 4 to the patient. Y-piece 5 is connected to the airway adapter 6, which includes sampling line connector 7. Then there is advantageously a filter 8, e.g. bacteria filter or heat and moisture exchanger, and an intubation tube 9. Breath gas measuring unit 3 draws a small amount of breathing air from the airway adapter 6 using a pump. Air flows through a sampling line 10 to the water trap 11, which removes water and mucus from the air.

Figure 2:
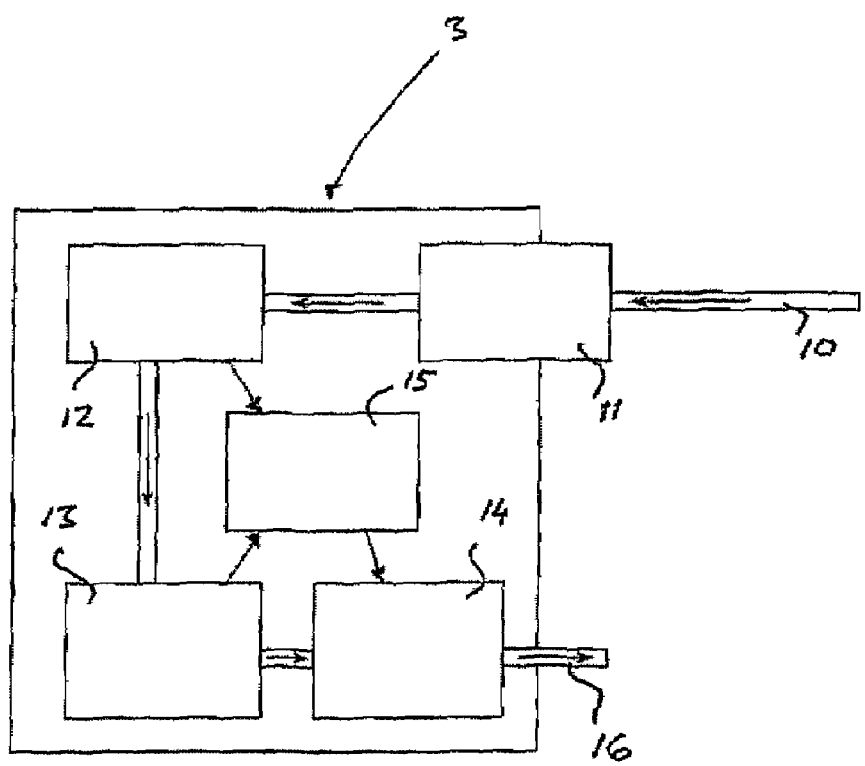
FIG. 2 shows a simplified principle of the breath gas measuring unit.

FIG. 2 shows a simplified principle of the breath gas measuring unit. The air flows through the sampling line 10 to the gas sensor 12, which measures one or more breath gases. Then there is a sample flow measurement unit 13 and a pump 14. A Central Processing Unit 15 (CPU) determines the gas concentrations based on the sensor signal(s). For example the sample flow measurement unit 13, the pump 14 and the CPU 15 described above form in this embodiment a flow control arrangement for adjusting the sample rate The CPU 15 determines the sample flow and controls the pump 14 according to the measurement result. In the example of FIG. 2 the pump 14 is used. The invention is however not restricted to a pump but instead of a pump it is quite possible to use any other appropriate device to create a vacuum effect for drawing the sample flow from the patient's breath flow to and through the gas measuring unit 3. In the example of FIG. 2 further the channels from water trap 11 through gas sensor 12, sample flow measurement 13 unit, and pump 14 are formed by internal tubing. Reference number 16 shows an output for gas.

Figure 3:
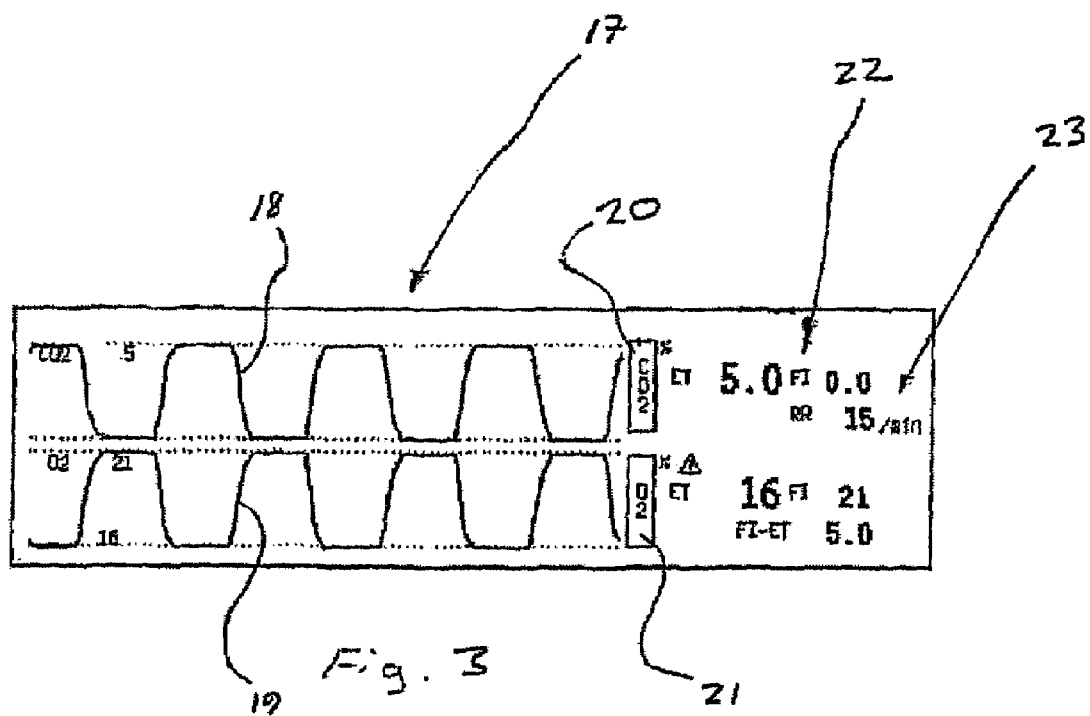
FIG. 3 shows one example of a medical monitor display showing the values measured.

The breath gas measuring unit 3 described in FIGS. 1 and 2 is connected to a medical monitor display 17, showing the gas curve(s), Et- and Fi-values of the measured gas(es) and respiration rate. Et-value (End tidal) describes gas content of the end of expiration, for example in connection with CO2 maximal content 5.2 vol-% and in connection with O2 normally minimal content for example 16 vol-%. Fi-value (Final inspiration) describes gas content of the end of inspiration, for example CO2 minimal content 0.0 vol-%. Respiration rate can e.g. be determined from ventilation settings and/or by measuring frequencies of gas concentration changes. FIG. 3 shows an example of the medical monitor 17 displaying CO2- and O2-curves and other information described above. In FIG. 3 reference numbers 18, 19 show gas waveform, i.e. CO2 and O2 curves, reference numbers 20, 21 show gas labels, reference number 22 shows a digit field for Et- and Fi-values, and reference number 23 shows respiration rate.

Figure 4:
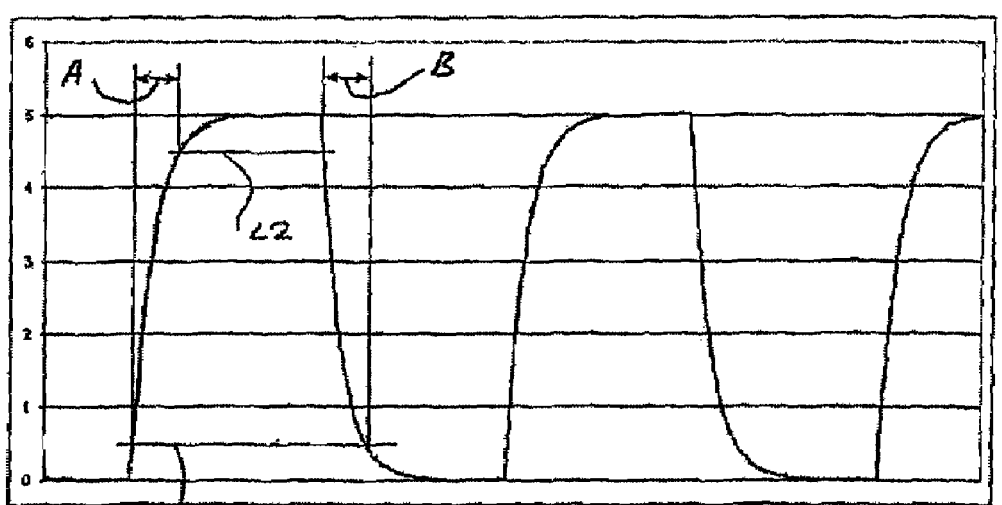
FIG. 4 shows gas curve and definition of rise and fall times.

As described above a normal way to implement sample flow control in a sidestream type respiratory gas monitor is to use a constant sample flow rate. The term constant sample flow rate means that regardless of the situation the sample flow rate is tried to keep constant. The amount of sample flow rate is determined to be high enough for the maximum specified breathing rate that the device is enabled to measure. The rise and fall time of the gas decreases when the sample flow decreases, which means that with high breathing rates also the sample flow rate should be high. The rise time is a time required to achieve a rise from 10% to 90% of final gas value when a step function change in gas concentration occurs at the sampling site. Fall time is a time from 90% to 10% of final gas value. The meaning of the terms rise time and fall time is clarified in FIG. 4 showing gas curve and definition of said terms. In the example of FIG. 4 line L1 shows the level of 10% of the final value and line L2 shows the level of 90% of the final value. Arrow A shows the rise time and arrow B shows the fall time.

In typical case breathing rate is much smaller than the maximum specified. The maximum breathing rate can be for example 100 breaths/min but in many cases the typical breathing rate is only 6-20 breaths/min specially if the patient is connected to the ventilator. Usually the curve display rate on the monitor display can be adjusted so that if the respiration rate is high, also the curve display rate is high and vice versa. With small breathing rates the respiratory gas monitor could produce a good breathing curve and excellent gas measurement accuracy (Et/Fi-values) with smaller sample flow rate because also the curve display rate on the monitor display is small.

The drawbacks in said constant sample flow rate technique are described earlier in the text when the prior art is discussed.

In the invention a new way to generate sample flowrate for the sidestream type breathing gas analyser is developed.

The invention is based on the fact that because with high respiration rates the high sample flow rate is needed and with low respiration rates the sample flow rate could be lower, the sample flow rate should be dynamically adjusted based on the respiration rate. That way several benefits could be achieved without sacrificing the measurement accuracy.

The minimum sample flow rate would be in use when the respiration rate is around 3-4 breaths/min or when no signal is detected. When the breathing rate gets higher also the sample flow rate gets bigger, and when the breathing rate gets lower the sample flow rate gets lower. The maximum sample flow rate is used with maximum specified breathing rate and also with higher breathing rates. The equation for the desired sample flow rate, if the breathing rate is known, has the form: Sample flow rate=X*breathing rate+minimum sample flow rate. X is a gain coefficient that has to be defined individually for every device type as well as the minimum sample flow rate so that in every respiration rate the breathing curve looks good and the measurement accuracy is the best possible. The specification for the sample flow rate could for example have a form "2-5 ml/breath".

The relationship between sample flow rate and breathing rate can be linear but it is not the only possibility. The relationship between sample flow rate and breathing rate can be also logarithmic, exponential, higher degree polynomial or whichever works best. The main issue is that the sample flow rate is adjusted if needed on the basis of the respiration rate of the patient, i.e. the sample flow rate is adjusted in case if the sample flow rate is not within limits set by the patient's breathing rate. The limits referred above can be for example ±5% of the ideal calculated sample flow rate. In addition of that the breath gas measuring unit 3 can measure the rise and fall time and take care that the curve has a right shape.

The embodiments of the invention are by no means intended to restrict the invention but only to clarify the basic idea of the invention. It is quite clear that details of the invention can be varied within the scope of the claims. For example the breath gas measuring unit can within the spirit of the invention be either a separate element or said gas measuring unit can be attached to the ventilator or alternatively said gas measuring unit can be an integral part of the ventilator or an integrated part of the monitor etc. The breath gas measuring unit can also be a detachable module. The embodiments described above are related to a ventilation procedure. The invention is however not restricted to the ventilation procedure but the invention can quite well be used in connection with a spontaneously breathing patient. This embodiment is basically the same as described in FIG. 1 but without ventilator 2 and breathing tubes 4. Intubation tube can be used in this embodiment but said intubation tube is not inevitable but the sampling line 10 can also be guided via nostril.

The invention claimed is:

1. Method for measuring breath gases of a patient, the method comprising following step:
   connecting the patient to a breath gas measuring unit by using a sampling line to enable flowing a sample of the breath gases of the patient with a pre-determined sample flow rate to the breath gas measuring unit for measurement of the sample, and
   adjusting the sample flow rate to within limits set by the patient's breathing rate.

2. The method of claim 1 wherein the relationship between the sample flow rate and the patient's breathing rate is linear.

3. The method of claim 1 wherein the relationship between the sample flow rate and the patient's breathing rate is logarithmic.

4. The method of claim 1 wherein the relationship between the sample flow rate and the patient's breathing rate is exponential.

5. The method of claim 1 wherein the relationship between the sample flow rate and the patient's breathing rate is higher degree polynomial.

6. The method of claim 1 wherein the sample flow rate is increased while the patient's respiration rate increases and decreased while the patient's respiration rate decreases.

7. The method of claim 1 wherein the method further comprises the step of connecting the patient to a ventilator by using ventilator tubes.

8. Arrangement for measuring breath gases of a patient which arrangement comprises a sampling line and a breath gas measuring unit, the sampling line being arranged to enable flowing a sample of the patient's breath gases with a pre-determined sample flow rate to the breath gas measuring unit for measurement of the sample, the breath gas measuring unit being provided with a flow control arrangement, wherein the flow control arrangement adjusts the sample flow rate to within limits set by the patient's breathing rate.

9. The arrangement of claim 8 wherein the breath gas measuring unit comprises a water trap for separating water and mucus from the sample of the patient's breath gases, a pump for enabling the flow of the sample of the breath gases from the patient through the sampling line to the breath gas measuring unit, a gas sensor for measuring the breath gas sample, a flow measurement unit for measuring sample flow and a CPU for analyzing the results measured and for controlling the pump for adjusting the sample flow.

10. The arrangement of claim 8 wherein the arrangement further comprises a medical monitor display showing essential measuring results.

11. The arrangement of claim 10 wherein the essential measuring results comprise the gas curves, Et- and Fi-values measured and respiration rate.

12. The arrangement of claim 11 wherein the breath gas measuring unit is arranged to measure the rise and fall time from the gas curve measured to take care that the curve has a right shape.

13. The arrangement of claim 8 wherein the arrangement further comprises a ventilator and ventilator tubes, the ventilator tubes being arranged to connect the patient to the ventilator.

14. The arrangement of claim 8, wherein that the flow control arrangement for adjusting the sample flow rate is arranged to increase the sample flow rate while the patient's respiration rate increases and to decrease the sample flow rate while the patient's respiration rate decreases.

* * * * *